United States Patent [19]

Harui

[11] Patent Number: 4,469,106
[45] Date of Patent: Sep. 4, 1984

[54] NEEDLE GUIDE FOR USE WITH MEDICAL ULTRASONIC SCANNING APPARATUS

[75] Inventor: Norio Harui, Seattle, Wash.

[73] Assignee: Advanced Technology Laboratories, Inc., Bellevue, Wash.

[21] Appl. No.: 433,931

[22] Filed: Oct. 12, 1982

Related U.S. Application Data

[63] Continuation-in-part of Ser. No. 414,141, Sep. 2, 1982, abandoned.

[51] Int. Cl.³ .............................................. A61B 10/00
[52] U.S. Cl. ..................................................... 128/660
[58] Field of Search .............................. 128/660–663, 128/303.19, 24 A, 754

[56] References Cited

U.S. PATENT DOCUMENTS

| | | | |
|---|---|---|---|
| 3,556,079 | 1/1971 | Omizo | 128/2 |
| 4,029,084 | 6/1977 | Soldner | 128/2 V |
| 4,058,114 | 11/1977 | Soldner | 128/2 V |
| 4,108,165 | 8/1977 | Kopp et al. | 128/2 V |
| 4,249,539 | 2/1981 | Vilkomerson et al. | 128/2 V |
| 4,289,139 | 9/1981 | Enjoji et al. | 128/660 |
| 4,402,324 | 9/1983 | Lindgren | 128/660 |

*Primary Examiner*—Kyle L. Howell
*Assistant Examiner*—Deidre A. Foley
*Attorney, Agent, or Firm*—Lawrence S. Levinson; Sanford J. Asman

[57] ABSTRACT

A needle guide for use with a medical ultrasonic scanning apparatus includes a pivoting plate on a fixed mounting plate. The mounting plate is attached to an ultrasonic scanhead whereby a surface of the mounting plate is in the plane of the ultrasound scan. An adjustable pivoting plate on the mounting plate includes at least one needle aligner, which preferably has a groove formed therein. The pivoting plate can be pivoted and locked into position on the mounting plate. An idler plate, containing an idler roller is spring mounted on the pivoting plate. The idler plate can be pivoted, whereby the idler roller moves away from the guide needle aligners. A raised wall on the pivoting plate prevents an improperly placed needle from puncturing a sterile sheath applied over the scanhead, such as in a brain scan. Thus a needle, such as a biopsy needle can be placed between the idler roller and the needle aligner and will be held in place by the spring tension on the idler roller.

16 Claims, 5 Drawing Figures

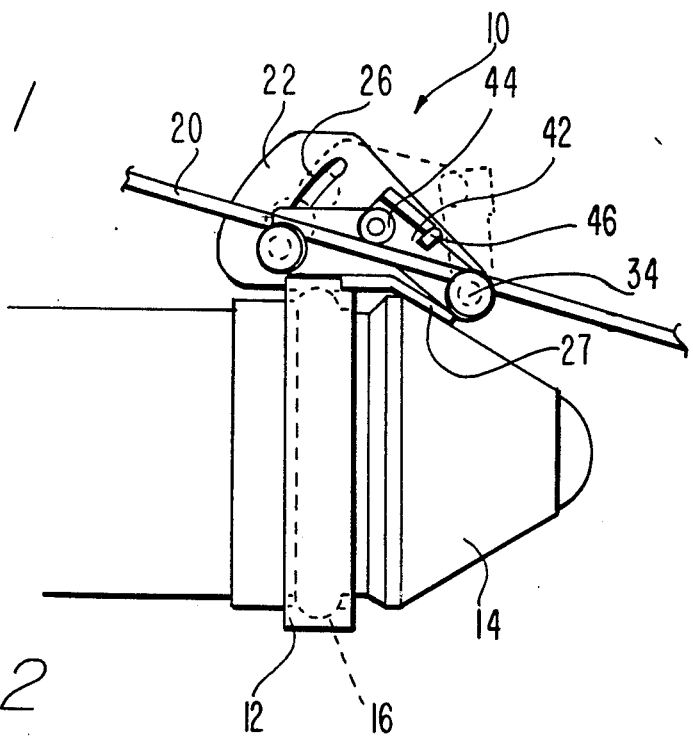
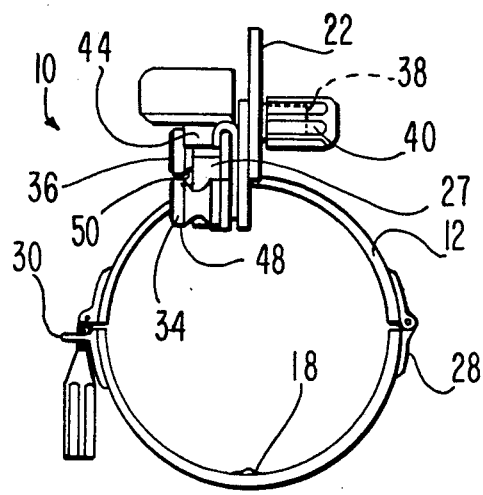
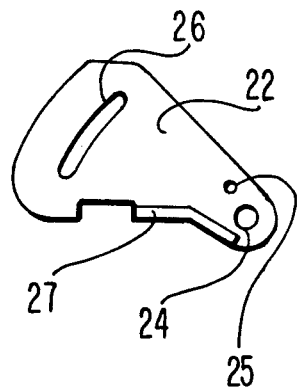

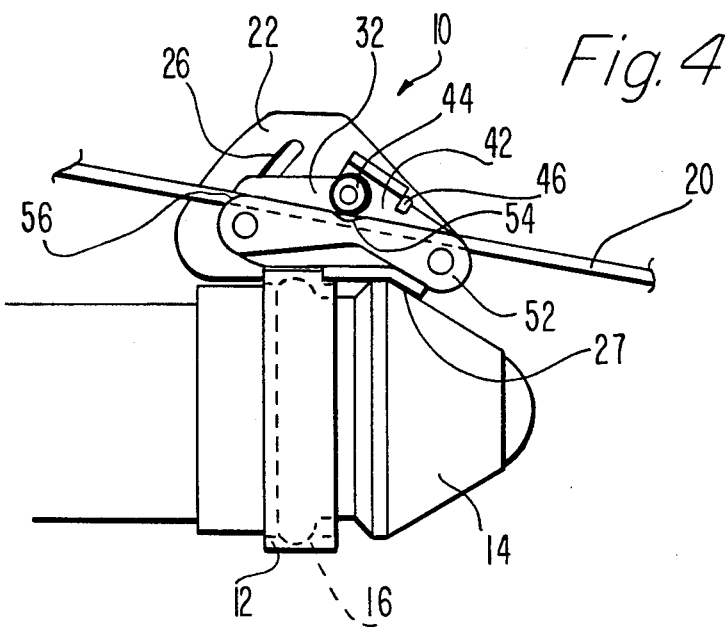
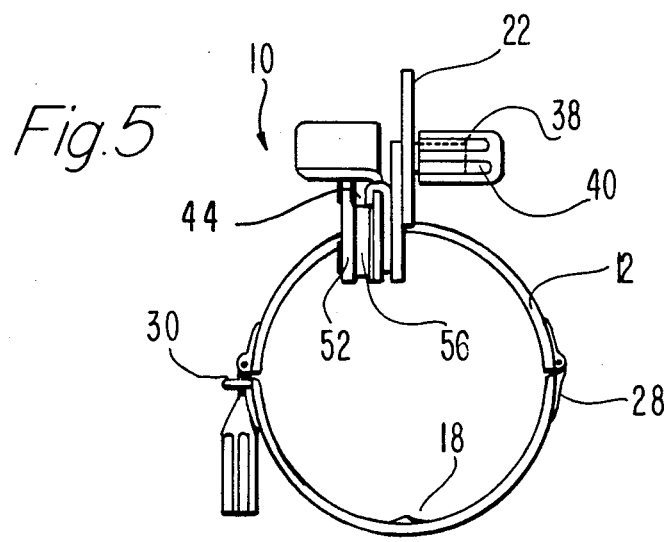

NEEDLE GUIDE FOR USE WITH MEDICAL ULTRASONIC SCANNING APPARATUS

BACKGROUND OF THE INVENTION

This is a continuation-in-part of U.S. Pat. application Ser. No. 414,141, filed Sept. 2, 1982, now abandoned.

The present invention relates to a needle guide for use with medical ultrasonic scanning apparatus. In particular, the present apparatus is a guide for a needle, such as a biopsy needle. The guide is intended to be mounted on an ultrasonic scanhead.

Heretofore, ultrasonic scanners, of the type used in medical diagnostic examinations have been well known. Such scanners are used to produce, on the screen of a cathode ray tube (CRT), a two-dimensional, cross-sectional image of a body region being scanned. Ultrasonic scanners are also used to aid in the insertion of needles during medical procedures, such as the aspiration of fluids from an interior body region or the performance of a biopsy. In such cases, the scanner interrogates the affected body region while the needle is being inserted, thereby producing on the screen of the CRT an image representing the relative positioning of the needle and the internal body structure of the region.

When an ultrasound scanner utilizes a rotating or oscillating transducer, the sector scan which is produced corresponds to a slice through the body portion taken in a plane corresponding to the axis of transmission and reception of ultrasound from the transducer. Thus, in order to observe a body organ into which a needle is being inserted, while at the same time observing the needle which is being inserted in order to accurately place it, it is necessary that the needle be inserted in the plane of the slice corresponding to the sector scan being produced. It would, therefore, be desirable to have a mounting bracket which could mount on an ultrasound scanhead which could hold a needle being inserted in the course of a medical procedure. It would also be desirable if the mounting bracket could be adjusted for various diameter needles and if it could also be adjusted to insert the needles at various angles, all the while providing for the insertion of the needle in the plane of the ultrasound scan. In addition, it would be desirable to produce such a guide apparatus which could be readily applied to or removed from the ultrasound scanhead.

SUMMARY OF THE INVENTION

In accordance with the present invention an adjustable needle guide for an ultrasound scanhead is provided. The needle guide can be readily applied over an ultrasound scanhead and latched securely in place on the scanhead. The needle guide mounting bracket is keyed to the ultrasound scanhead in a manner which assures that a needle inserted into the guide will be in the plane of the ultrasound scan produced by the scanhead. The needle guide contains means for securely holding and easily inserting a needle of various diameters. in addition, the guide includes adjustable means for fixing, in an adjustable manner, the angle at which the needle enters the patient.

The adjustable needle guide for use with a medical ultrasonic scanning apparatus comprises a mounting plate including means for attachment to an ultrasonic scanning apparatus. It further comprises a pivoting plate, pivotally mounted on said mounting plate, whereby the pivoting plate can be moved in the plane of the ultrasonic scan. The pivoting plate includes means for locking it in a fixed angular position on the mounting plate. Needle aligner means, including at least one needle aligner is mounted on the pivoting plate. The needle aligner means is adapted to slideably hold a needle which is biased against the needle aligner means. An idler plate is pivotally mounted on the pivoting plate. The idler plate includes an adjustable needle diameter biasing means. Finally, the device includes spring means which biases the idler plate to move the adjustable needle diameter biasing means toward the needle aligner means on the pivoting plate, whereby a needle placed between the needle aligner means and the adjustable needle diameter biasing means is biased toward the needle aligner means by the spring means.

BRIEF DESCRIPTION OF THE DRAWING

In the drawing:

FIG. 1 is a top view of a first embodiment of the guide of the present invention mounted on an ultrasound scanhead;

FIG. 2 is a front view of the needle guide of FIG. 1;

FIG. 3 is a top view of the mounting plate of the needle guide;

FIG. 4 is a top view of a second embodiment of the guide of the present invention mounted on an ultrasound scanhead; and FIG. 5 is a front view of the needle guide of FIG. 4.

DETAILED DESCRIPTION OF THE PREFERRED EMBODIMENTS

Referring generally to FIGS. 1 and 2, a first embodiment of the needle guide 10 of the preferred embodiment of the invention, is shown. With particular reference to FIG. 1, the needle guide 10 is shown mounted, using a clamping ring 12 onto an ultrasound scanhead 14 of the type generally known in the art. In particular, the ultrasound scanhead may be a Model 725 scanhead of the type made by Advanced Technology Laboratories, Inc. of Bellevue, Wash. The ultrasound scanhead 14 includes a rounded shoulder 16 (shown in shadow in FIG. 1). At one point in the circumference in the shoulder 16 there is a notch which matches a keyed portion 18 (shown in FIG. 2) on the clamp 12. Thus, when the needle guide 10 is mounted on the scanhead 14, it will always be mounted in a keyed manner. Thus, as will be seen hereafter, the needle 20 which is held by the guide 10 will always be aligned in the plane of the ultrasound scan produced by the scanhead 14.

The needle guide 10 is comprised of a mounting plate 22, shown in FIG. 3. The mounting plate 22 is substantially triangular in shape. It includes a pivot hole 24 at the apex of the triangle and an arcuate opening 26 at the base of the triangle. The mounting plate 22 is attached to the clamp 12. The clamp 12 includes a hinge 28 and closing means, such as a screw mechanism 30. In alternative embodiments of the invention, the screw mechanism 30 can be replaced by a clasp rather than the screw type mechanism 30 shown in FIG. 2.

The needle guide 10 further comprises a pivoting plate 32. The pivoting plate 32 is mounted on the top surface of the mounting plate 22, as shown in FIGS. 1 and 2. The pivoting plate 32 has a pair of needle aligners 34, 36 mounted on its upper surface. In the preferred embodiment of the invention, the needle aligners are V-grooved rollers 34, 36, as shown. However, non-rolling needle aligners could be used instead of the rollers 34, 36. A threaded rod 38 (shown in shadow in FIG. 2) extends through the curved, arcuate opening 26 in the mounting plate 22. A knurled knob 40 is screwed onto the threaded rod 38 in a manner that allows it to be tightened onto the mounting plate 22, whereby the pivoting plate 32 can be locked in any position. Thus, the needle aligners 34, 36 which are mounted on the pivoting plate 22, determine the angle at which the needle 20 enters the patient, as shown in FIG. 1. By loosening the knurled knob 40 and adjusting the angle of the pivoting plate 32, the position of the pair of needle aligners 34, 36, relative to the scanhead 14, is adjusted.

An idler plate 42 is spring mounted on top of the pivoting plate 32. The idler plate 42 has, on its upper surface, an adjustable needle diameter biasing means, such as idler roller 44 used in the preferred embodiment of the invention. The idler plate 42 is biased by a spring 46, whereby the idler roller 44 tends to push on one side of the needle 20 while the two needle aligners 34, 36 on the pivoting plate 32 hold the needle 20 in a fixed position. One end of the spring is held in spring mounting hole 25, shown in FIG. 3.

In the preferred embodiment of the invention, the pair of needle aligners 34, 36 on the pivoting plate 32 include grooved portions 48, 50, as shown in FIG. 2, into which the needle 20 is urged by the idler roller 44. The arrangement of the idler plate 42 in combination with the spring loaded idler roller 44 and the fixed, grooved needle aligners 34, 36 on the pivoting plate 32 provides an automatically adjusting apparatus which can hold needles of various diameters. In addition, the particular arrangement used in the present invention provides for "no hands" needle threading and full visibility of the needle 20 at all times. Thus, a needle can be readily inserted or removed from the needle guide 10, and no needle size adjustment is required. The freely pivoting needle aligners 34, 36, and the idler guide 44 provide for a very low friction holding apparatus for the needle 20 which means that a doctor using the present invention can retain full tactile control over the needle 20 at all times.

A safety feature of the preferred embodiment of the invention is a raised wall 27 which prevents someone from inadvertently puncturing the sterile sheath which typically covers a scanhead 14 during a brain scan or a similar procedure. In operation, the raised wall 27 acts to deflect a needle 20 which is not properly placed between the needle aligners 34, 36 and the idler roller 44 away from the scanhead 14.

Referring now to FIGS. 4 and 5, a second embodiment of the needle guide 10 of the preferred embodiment of the invention, is shown. The needle guide 10 of the second embodiment, shown in FIGS. 4 and 5, is substantially identical to the needle guide described with reference to FIGS. 1-3. Accordingly, like reference numerals have been used in FIGS. 4 and 5 to describe like parts, and no further description of those parts will be provided.

In this embodiment of the needle guide 10, there is a single, elongated needle aligner 52 mounted on the upper surface of the pivoting plate 32. The elongated needle aligner 52 replaces the pair of needle aligners 34, 36 used in the first embodiment, described with reference to FIGS. 1 and 2. In this embodiment of the invention, the needle aligner 52 includes a V-groove 56. There is an arcuate opening 54 in the needle aligner 56 which permits the idler roller 44 to bias the a needle 20 into the V-groove 56. As will be recognized by those skilled in the art, in this embodiment of the invention, a narrow diameter, relatively flexible needle 20 will be supported along a greated portion of its length than it would have been supported along using the first embodiment of the invention. In particular, it will be supported where it is contacted by the idler roller 44. Accordingly, using this embodiment of the invention, a flexible needle 20 will be prevented from bowing. That might not be the situation using the embodiment of the invention shown in FIGS. 1 and 2 which includes two needle aligners 34, 36 on the pivoting plate 32.

As will be understood by those skilled in the art, either embodiment of the present invention provides two distinct adjustment means. First, the angle of the needle 20 is adjustable, based upon changing the angle of the pivoting plate 32 relative to the mounting plate 22. Second, the spring biased idler plate 42, with its idler guide 44, together with the needle aligners 34, 36 on the pivoting plate 32, provides an automatic adjustment means for different diameter needles.

I claim:

1. An adjustable needle guide for use with a medical ultrasonic scanning apparatus comprising:
   (a) A mounting plate including means for attachment to an ultrasonic scanning apparatus;
   (b) A pivoting plate, pivotally mounted on said mounting plate, whereby said pivoting plate can be moved in the plane of the ultrasonic scan, said pivoting plate including means for locking said pivoting plate in a fixed angular position on said mounting plate;
   (c) At least one needle aligner mounted on said pivoting plate, said at least one needle aligner being adapted to slideably hold a needle which is biased against said needle aligner;
   (d) An idler plate which is pivotally mounted on said pivoting plate, said idler plate including an adjustable needle diameter biasing means; and
   (e) Spring means which biases said idler plate to move said adjustable needle diameter biasing means toward said at least one needle aligner on said pivoting plate, whereby a needle placed between said at least one needle aligner and said adjustable needle diameter biasing means is biased toward said at least one needle aligner by said spring means.

2. The adjustable needle guide of claim 1 wherein said means for attachment of said mounting plate to said ultrasonic scanning apparatus includes means for aligning said mounting plate in the plane of the scan of said ultrasonic scanning apparatus.

3. The adjustable needle guide of claim 1 comprising a pair of needle aligners.

4. The adjustable needle guide of claim 3 wherein said needle aligners are comprised of rollers, the axis of rotation of said needle aligners being substantially orthogonal to the surface of said pivoting plate.

5. The adjustable needle guide of claim 3 wherein said mounting plate further comprises a raised protective wall between said needle aligners and said scanhead, whereby a needle will be deflected away from said scanhead if it is not properly placed between said needle aligners and said adjustable needle diameter biasing means.

6. The adjustable needle guide of claim 3 wherein said adjustable needle diameter biasing means comprises an idler roller, the axis of rotation of said idler roller being substantially orthogonal to the surface of said idler plate.

7. The adjustable needle guide of claim 6 wherein said needle aligners are comprised of rollers, the axis of rotation of said needle aligners being substantially orthogonal to the surface of said pivoting plate.

8. The adjustable needle guide of claim 7 wherein said ultrasonic scanning apparatus is a mechanical sector scanner and said means for attachment of said mounting plate to said ultrasonic scanning apparatus includes a band which encircles one end of said ultrasonic scanning apparatus.

9. The adjustable needle guide of claim 8 wherein said means for aligning said mounting plate in the plane of the scan of said ultrasonic scanning apparatus includes a key on said band.

10. The adjustable needle guide of claim 1 wherein said ultrasonic scanning apparatus is a mechanical sector scanner and said means for attachment of said mounting plate to said ultrasonic scanning apparatus includes a band which encircles one end of said ultrasonic scanning apparatus.

11. The adjustable needle guide of claim 1 wherein said means for aligning said mounting plate in the plane of the scan of said ultrasonic scanning apparatus includes a key on said band.

12. The adjustable needle guide of claim 1 comprising a single needle aligner.

13. The adjustable needle guide of claim 12 wherein said needle aligner is comprised of a single, elongated piece.

14. The adjustable needle guide of claim 13 wherein said needle aligner includes a groove adapted to receive a needle, said groove extending along the length of said needle aligner in an axis substantially orthogonal to the axis of rotation of said idler roller.

15. The adjustable needle guide of claim 14 wherein said ultrasonic scanning apparatus is a mechanical sector scanner and said means for attachment of said mounting plate to said ultrasonic scanning apparatus includes a band which encircles one end of said ultrasonic scanning apparatus.

16. The adjustable needle guide of claim 15 wherein said means for aligning said mounting plate in the plane of the scan of said ultrasonic scanning apparatus includes a key on said band.

* * * * *